(12) United States Patent
Merslavic et al.

(10) Patent No.: US 7,674,814 B2
(45) Date of Patent: Mar. 9, 2010

(54) PROCESS FOR THE PREPARATION OF PERINDOPRIL AND SALTS THEREOF

(75) Inventors: Marjo Merslavic, Straza pri Novem mestu (SI); Janja Smid, Novo mesto (SI); Zdenka Tomsic, Novo mesto (SI)

(73) Assignee: Les Laboratoires Servier, Neuilly sur Seine (FR)

( * ) Notice: Subject to any disclaimer, the term of this patent is extended or adjusted under 35 U.S.C. 154(b) by 20 days.

(21) Appl. No.: 11/568,908

(22) PCT Filed: May 10, 2005

(86) PCT No.: PCT/EP2005/005048

§ 371 (c)(1), (2), (4) Date: Jan. 16, 2007

(87) PCT Pub. No.: WO2005/113500

PCT Pub. Date: Dec. 1, 2005

(65) Prior Publication Data

US 2008/0051584 A1  Feb. 28, 2008

(30) Foreign Application Priority Data

May 14, 2004  (SI)  ............... 200400143
Aug. 5, 2004  (SI)  ............... 200400235

(51) Int. Cl.
*A61K 31/403* (2006.01)
(52) U.S. Cl. .................................. 514/412
(58) Field of Classification Search ............. 514/412
See application file for complete search history.

(56) References Cited

U.S. PATENT DOCUMENTS

| | | | |
|---|---|---|---|
| 4,350,704 A | 9/1982 | Hoefle et al. |
| 4,425,355 A | 1/1984 | Hoefle et al. |
| 4,508,729 A | 4/1985 | Vincent et al. |
| 4,902,817 A | 2/1990 | Vincent et al. |
| 4,914,214 A | 4/1990 | Vincent et al. |
| 4,935,525 A | 6/1990 | Vincent et al. |
| 4,954,640 A | 9/1990 | Vincent et al. |
| 5,258,525 A | 11/1993 | Maryanoff et al. |
| 5,350,582 A | 9/1994 | Merslavic |
| 6,602,880 B2 | 8/2003 | Schoen et al. |
| 6,653,336 B1 | 11/2003 | Guez et al. |
| 6,696,481 B2 | 2/2004 | Damien et al. |
| 6,774,259 B2 | 8/2004 | Souvic et al. |
| 6,818,788 B2 | 11/2004 | Souvic et al. |
| 6,835,843 B2 | 12/2004 | Langlois et al. |
| 7,157,484 B2 | 1/2007 | Dubuffet et al. |
| 2003/0137067 A1 | 7/2003 | Cooper et al. |
| 2003/0158121 A1 | 8/2003 | Pfeiffer et al. |
| 2003/0186896 A1 | 10/2003 | Pfeiffer et al. |
| 2003/0232796 A1 | 12/2003 | Cooper et al. |
| 2004/0029813 A1 | 2/2004 | Pfeiffer et al. |
| 2004/0248817 A1 | 12/2004 | Pfeiffer et al. |
| 2005/0059609 A1 | 3/2005 | Pfeiffer et al. |
| 2005/0119492 A1 | 6/2005 | Simig et al. |
| 2005/0142196 A1 | 6/2005 | Patel et al. |
| 2005/0203165 A1 | 9/2005 | Pfeiffer et al. |
| 2006/0252958 A1 | 11/2006 | Breard et al. |
| 2006/0276659 A1 | 12/2006 | Datta et al. |
| 2007/0172524 A1 | 7/2007 | Klobcar et al. |

FOREIGN PATENT DOCUMENTS

| | | |
|---|---|---|
| DE | 197 21 290 | 12/1997 |
| EP | 049658 | 6/1984 |
| EP | 037231 | 1/1987 |
| EP | 0308341 | 12/1990 |
| EP | 0308340 | 3/1991 |
| EP | 0309324 | 3/1991 |
| EP | 0308339 | 5/1992 |
| EP | 280 999 | 1/1993 |
| EP | 1338591 | 8/2003 |
| EP | 1362845 | 11/2003 |
| EP | 1323729 | 11/2004 |
| EP | 1403278 | 6/2005 |
| EP | 1400531 | 1/2006 |
| GB | 2394660 | 5/2004 |
| WO | WO 9925374 A1 | 5/1999 |
| WO | WO 01/56353 | 8/2001 |
| WO | WO 01/56972 | 8/2001 |
| WO | WO 01/58868 | 8/2001 |
| WO | WO 01/83439 | 11/2001 |
| WO | WO 01/87835 | 11/2001 |
| WO | WO 01/87836 | 11/2001 |
| WO | WO 03/059388 | 7/2003 |
| WO | WO 03/064388 | 8/2003 |
| WO | WO 03/075842 | 9/2003 |
| WO | WO 03/087050 | 10/2003 |
| WO | WO 2004/075889 | 9/2004 |
| WO | WO 2005/011737 | 2/2005 |

OTHER PUBLICATIONS

Hanson, James R. Organic Synthetic Methods. Oct. 2003, Publisher: Wiley, John, and Son, Incorporated, pp. 130-131.*
Tetrahedron Lett. (1982) 23(16):1677-1680.
Drug Design and Discovery (1992) 9(1):11-28.
http://www.signetchem.com, Avicel PH(R)- Microcrystalline Cellulose, 2002, http://www.signetchem.com/product/avicelph.htm,2 pages.

(Continued)

*Primary Examiner*—Rebecca L Anderson
*Assistant Examiner*—Shawquia Young
(74) *Attorney, Agent, or Firm*—Swanson & Bratschun, L.L.C.

(57) ABSTRACT

The present invention relates to a process for the preparation of the ACE inhibitor (2S,3aS,7aS)-1-((2S)-2-(((1S)-1-(ethoxycarbonyl)butyl)amino)-1-oxopropyl)octahydro-1H-indol-2-carboxylic acid and of pharmaceutically acceptable salts thereof as well as to intermediates useful in said process.

5 Claims, No Drawings

OTHER PUBLICATIONS http://www.signetchem.com, Avicel PH-101(R)- Microcrystalline Cellulose, 2002, http://www.signetchem.com/pdf/FMC/Avicel%20PH-101.pdf, 1 page.

http://www.fmcbiopolymer.com, Avicel PH(R)-102- Microcrystalline Cellulose, 2002, http://www.fmcbiopolymer.com/Portals/Pharm/Content/Docs/avicelhfemsds.pdf, 9 pages.

http://www.signetchem.com, Avicel (R)PH-103- Microcrystalline Cellulose, 2002, http://www.signetchem.com/pdf/FMC/Avicel%20PH-103.pdf, 1 page.

http://www.signetchem.com, Avicel PH(R)-301- Microcrystalline Cellulose, 2002, http://www.signetchem.com/pdf/FMC/Avicel%20PH-301.pdf, 1 page.

http://www.signetchem.com, Avicel PH(R)-112- Microcrystalline Cellulose, 2002, http://www.signetchem.com/pdf/FMC/Avicel%20PH-112.pdf, 1 page.

Vippagunta et al., Crystalline Solids, 2001, Advanced Drug Delivery Reviews, 48:3-26.

* cited by examiner

PROCESS FOR THE PREPARATION OF PERINDOPRIL AND SALTS THEREOF

RELATED APPLICATIONS

This application is a 35 U.S.C. §371 national phase application of PCT/EP2005/005048 (WO 2005/113500), filed on May 10, 2005, entitled "Processes For The Preparation of Perindopril and Salts Thereof" which claims priority to Slovenia Application Serial No. P-200400143, filed May 14, 2004 and Slovenia Application Serial No. P-200400235, filed Aug. 5, 2004. Each of these applications is specifically incorporated herein by reference in its entirety.

The present invention relates to the field of organic chemistry and relates to a process for the preparation of perindopril and to a salt as an intermediate used in its synthesis.

Perindopril, preferably the a t-butylamine salt thereof, is a compound having ACE inhibitory action.

There exists a need for an improved process for perindopril synthesis to be used on an industrial scale, whereby high yields and a high purity grade of the final product without undesired by-products can be achieved.

Perindopril with the chemical name (2S,3aS,7aS)-1-((2S)-2-(((1S)-1-(ethoxycarbonyl)butyl)amino)-1-oxopropyl) octahydro-1H-indol-2-carboxylic acid is disclosed in EP 49 658. The described synthesis is a multi-step process and includes separation of isomers by column chromatography.

EP 308 341 teaches an improved large-scale synthesis of perindopril in the form of the t-butylamine salt. (2S,3aS,7aS)-octahydroindole-2-carboxylic acid benzyl ester p-toluensulfonic salt and N-((S)-1-carbethoxybutyl)-L-alanine are reacted in the presence of triethyl amine, N,N-dicyclohexylcarbodiimide and 1-hydroxybenztriazole. After completion of the reaction, perindopril benzyl ester is obtained, which is reduced, lyophilized and then converted into a salt with t-butylamine in ethyl acetate.

In WO 01/58868 the use of a lower ratio of (2S,3aS,7aS)-octahydroindole-2-carboxylic acid benzyl ester p-toluensulfonic salt, N-((S)-1-carbethoxybutyl)-L-alanine, triethyl amine, N,N-dicyclohexylcarbodiimide and 1-hydroxybenztriazole is disclosed in order to reduce the formation of by-products of the reaction between perindopril benzyl ester and N,N-dicyclohexylcarbodiimide. Despite the lower ratio, by-products are still present.

In WO 03/064388 a synthesis of perindopril without by-products of the reaction with N,N-dicyclohexylcarbodiimide is disclosed. The reaction takes place between (2S,3aS,7aS)-octahydroindole-2-carboxylic acid and N-acyl protected N-((S)-1-carbethoxybutyl)-L-alanine chloride. The acid chloride is prepared by using thionyl chloride and previously protected N-((S)-1-carbethoxybutyl)-L-alanine. A disadvantage of said process is a low yield obtained after the condensation and removal of the protecting group, namely 35 to 55% only.

It has now surprisingly been found that by the present invention directed to a perindopril synthesis using unprotected N-((S)-1-carbethoxybutyl)-L-alanine in form of its acid chloride or salt of the acid chloride the above-mentioned disadvantages are avoided.

The main advantages of the present invention are the providing of perindopril of high quality and purity in a high reaction yield without by-products.

DETAILED DESCRIPTION OF THE INVENTION

The invention is first of all directed to a process for the preparation of perindopril of the formula I or of pharmaceutically acceptable salts thereof

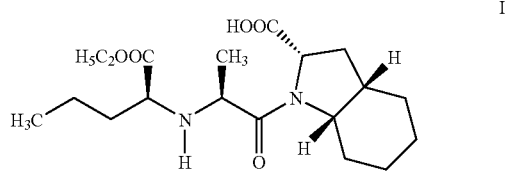

characterized in that the acid chloride of the formula III or a salt thereof

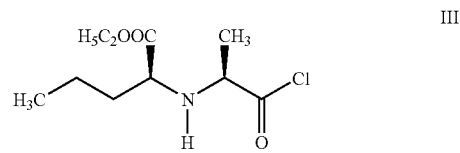

is reacted with (2S,3aS,7aS)-octahydroindole-2-carboxylic acid of the formula IV

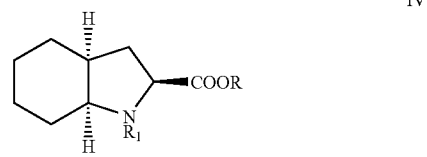

wherein R represents a protecting group, such as benzyl, t-butyl, trimethylsilyl group, or hydrogen or a cation, such as potassium, lithium or sodium, and $R_1$ represents hydrogen or a protecting group, such as the trimethylsilyl group, to a compound of the formula V

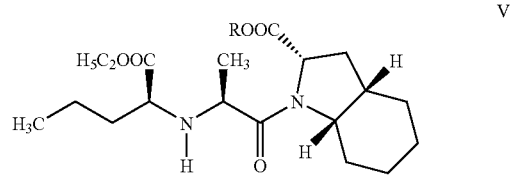

wherein R has the above meaning, which, when R is not hydrogen, is converted to perindopril of the formula I by hydrogenolysis or hydrolysis.

Subsequent to this reaction, a conversion into a desired salt of perindopril may be accomplished.

It is preferred that R is not benzyl in the specific case of the reaction of acid chloride of the formula III with (2S,3aS,7aS)-octahydroindole-2-carboxylic acid of the formula IV.

It is also preferred that the acid chloride of the formula III

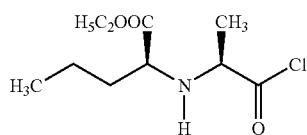

is prepared by conversion of N-((S)-1-carbethoxybutyl)-L-alanine of the formula II

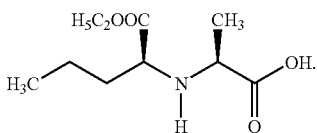

It has also been shown to be advantageous to use in the process of the invention a salt of the acid chloride of the formula III and preferably the hydrochloride salt. These salts can be more easily purified than the compound III as such so that a highly pure starting material can be used. This also results in a more pure final product.

The condensation reaction, i.e. the formation of a peptide bond between the compound of the formula III and the compound of the formula IV, takes preferably place in organic solvents, such as acetone, acetonitrile, dioxan, chloroform, methylene chloride, tetrahydrofuran or optionally in a combination thereof with water, and preferably in the presence of a base, in the temperature range of from −20° C. to +20° C., preferably at a temperature of from 0° C. to −20° C.

The compound of the formula I and pharmaceutically acceptable salts thereof are isolated by known or conventional processes. The compound may be isolated in the form of the t-butylamine salt that is known from EP 308 341 and may occur in various polymorphic forms such as are e.g. disclosed in WO 01/87835 (alpha polymorph), WO 01/87836 (beta polymorph) and WO 01/83439 (gamma polymorph).

The compound I may also be isolated in the form of other pharmaceutically acceptable salts such as e.g. arginine salt disclosed in WO 03/087050.

The invention also relates to the compound of the formula III

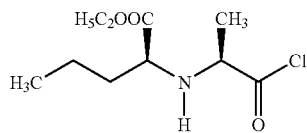

in form of a salt thereof. Such a salt is preferably the hydrochloride salt.

The salt according to the invention can be prepared by a corresponding conversion of compound III.

However, it is also possible to prepare it directly from compounds of the formula II in salt form, preferably in the hydrochloride form.

The hydrochloride of the compound of the formula II is described in Tetrahedron Lett. 1982, 23 (16) 1677-1680, Drug Design and Discovery 1992, 9 (1) 11-28, and EP 1 403 278.

It is preferred to convert compound II in a first step, e.g. with HCl in dichloromethane, into a salt thereof and then to convert this salt into the salt according to the invention of compound III.

The compound of the formula III can be prepared from N-((S)-1-carbethoxybutyl)-L-alanine, i.e. compound II, with reactants for preparing chlorides, such as phosphorus pentachloride, phosphorus trichloride, phosphoryl chloride or thionyl chloride. For preparing the chloride a 10 to 50% excess of the reactant may be used, the reaction is usually carried out in an inert solvent such as methylene chloride, in the temperature range of from −30° C. to 30° C., preferably at 0° C. to 10° C.

The compound of the formula III in salt form, preferably in hydrochloride form, may be isolated by partly evaporating the solvent and precipitating with an anti-solvent, such as different ethers or hydrocarbons.

Further, the invention also relates to a process for the preparation of perindopril or pharmaceutically acceptable salts thereof, wherein the salt according to the invention is used.

Finally, the invention relates also to the use of the salt according to the invention for the preparation of perindopril or pharmaceutically acceptable salts thereof.

Publications relating to reagents used in the above processes are given hereinafter.

The L-alanine derivative of the formula II is disclosed in EP 308 340, EP 308 341, EP 309 324, EP 1 362 845, EP 1 400 431, EP 1 400 531, WO 01/56353 and WO 01/56972.

Octahydroindole-2-carboxylic acid of the formula IV is well-known from EP 37231, EP 308339, EP 308341, EP 1323729, U.S. Pat. No. 5,258,525 and EP 1338591.

The present invention is illustrated, but not limited by the following Examples.

EXAMPLES

Example 1

Preparation of N-((S)-1-carbethoxybutyl)-L-alanyl chloride hydrochloride

To a suspension of N-((S)-1-carbethoxybutyl)-L-alanine (13.2 g) in dichloromethane (80 ml) HCl was introduced under stirring at 20-25° C. until a clear solution was obtained. The clear solution was cooled to −5° C. to 0° C., $PCl_5$ (12.9 g) was added and the stirring was continued at the same temperature for another five hours. Approximately one half of dichloromethane was evaporated from the suspension, diisopropyl ether (180 ml) was added and the stirring was continued at a temperature of from 10-25° C. for another hour. The precipitated crystals were filtered off and washed with diisopropyl ether (90 ml).

N-((S)-1-carbethoxybutyl)-L-alanyl chloride hydrochloride (15.1 g) was obtained.

Melting range=89-98° C. (decomposition)

IR ($cm^{-1}$): 2972, 1793, 1742, 1470 and 1206.

1H NMR (300 MHZ, DMSO-$d_6$) δ 0.90 (3H, t, J=7.15 Hz), 1.24 (3H, t, J=7.14 Hz), 1.40 (2H, m), 1.51 (3H, d, J=7.14 Hz), 1.86 (2H, m), 4.07 (2H, m), 4.21 (2H, m, J=7.14 Hz), and 9.71 (2H, b).

Example 2

Preparation of perindopril erbumin ((2S,3aS,7aS)-1-((2S)-2-(((1S)-1-(ethoxycarbonyl)butyl)amino)-1-oxopropyl)octahydro-1H-indol-2-carboxylic acid 2-methylpropane-2-amine salt)

Trimethylchlorosilane (2.86 ml) and triethyl amine (3.08 ml) were added to (2S,3aS,7aS)-octahydroindole-2-carboxylic acid (3.72 g) in dichloromethane (60 ml) at 20-25° C. and stirred at 20-25° C. for two hours. After two hours triethyl amine (2.8 ml) was added, the suspension was cooled to −15° C., a suspension of N-((S)-1-carbethoxybutyl)-L-alanyl chloride hydrochloride (5.5 g) in dichloromethane (60 ml), which has been cooled to −15° C., was poured thereto and the stirring was continued at −15° C. for two hours. The reaction solution was heated to 0° C., brine (25 ml) with dissolved NaOH (0.8 g) was added, and the pH was adjusted to 4.2 with a 20% NaOH solution. The organic phase was separated and the aqueous layer was once more washed with dichloromethane (20 ml). The combined dichloromethane layers were evaporated, the residue was dissolved in ethyl acetate (100 ml), the undissolved part was filtered off and t-butylamine (2.2 ml) was added to the filtrate. The precipitated crystals were dissolved at the boiling point of the solution, the clear solution was cooled to 10-20° C. and the stirring was continued for two hours. After two hours the precipitated crystals were filtered off, washed with ethyl acetate (12 ml) and dried at 35-40° C. in an air drier.

Perindopril erbumin (7.1 g; 80%) in an α form having a purity over 99% was obtained with individual impurities present in not more than 0.1% each.

Example 3

Preparation of perindopril erbumin from isopropyl acetate ((2S,3aS,7aS)-1-((2S)-2-(((1S)-1-(ethoxycarbonyl)butyl)amino)-1-oxopropyl)octahydro-1H-indol-2-carboxylic acid 2-methylpropane-2-amine salt)

Trimethylchlorosilane (2.92 ml) and triethyl amine (3.2 ml) were added to (2S,3aS,7aS)-octahydroindole-2-carboxylic acid (3.72 g) in dichloromethane (40 ml) at 20-25° C. and it was stirred at 20-25° C. for two hours. After two hours triethyl amine (2.77 ml) was added, the suspension was cooled to −15° C., a suspension of N-((S)-1-carbethoxybutyl)-L-alanyl chloride hydrochloride (5.5 g) in dichloromethane (80 ml), which had been cooled to −15° C., was poured thereto and the stirring was continued at −15° C. for two hours. The reaction solution was heated to 0° C., the precipitated triethylamine hydrochloride was filtered off and washed with dichloromethane (10 ml), water (33 ml), wherein NaOH (0.8 g) had been dissolved, was added to the filtrate, and the pH was adjusted to 4.2 with a 20% NaOH solution. The organic phase was separated and the aqueous layer was washed with dichloromethane (2×20 ml). The combined dichloromethane layers were evaporated, the residue was dissolved in isopropyl acetate (125 ml), the undissolved part was filtered off and t-butylamine (2.2 ml) was added to the filtrate. The precipitated crystals were dissolved at the boiling point of the solution, the clear solution was cooled to 10-20° C. and the stirring was continued for two hours. After two hours the precipitated crystals were filtered off, washed with isopropyl acetate (15 ml) and dried at 35-40° C. in an air drier.

Perindopril erbumin (7.65 g; 86%) in an α form having a purity over 99% was obtained with individual impurities present in not more than 0.1% each.

Example 4

Preparation of perindopril erbumin from N,N-dimethylformamide ((2S,3aS,7aS)-1-((2S)-2-(((1S)-1-(ethoxycarbonyl)butyl)amino)-1-oxopropyl)octahydro-1H-indol-2-carboxylic acid 2-methylpropane-2-amine salt)

Trimethylchlorosilane (2.92 ml) and triethyl amine (3.2 ml) were added to (2S,3aS,7aS)-octahydroindole-2-carboxylic acid (3.77 g) in dichloromethane (40 ml) at 20-25° C. and stirred at 20-25° C. for two hours. After two hours triethyl amine (2.77 ml) was added, the suspension was cooled to −15° C., a suspension of N-((S)-1-carbethoxybutyl)-L-alanyl chloride hydrochloride (5.5 g) in dichloromethane (40 ml), which had been cooled to −15° C., was poured thereto and the stirring was continued at −15° C. for two hours. The reaction solution was heated to 0° C., the precipitated triethylamine hydrochloride was filtered off and washed with dichloromethane (10 ml), water (33 ml), wherein NaOH (0.8 g) had been dissolved, was added to the filtrate, and the pH was adjusted to 4.2 with a 20% NaOH solution. The organic phase was separated and the aqueous layer was washed with dichloromethane (2×20 ml). The combined dichloromethane layers were evaporated, the residue was dissolved in N,N-dimethylformamide (90 ml), the undissolved part was filtered off and t-butylamine (2.2 ml) was added to the filtrate. The precipitated crystals were dissolved at 80° C., the clear solution was cooled to 10-20° C. and the stirring was continued for two hours. After two hours the precipitated crystals were filtered off, washed with N,N-dimethylformamide (9 ml) and dried at 35-40° C. in an air drier.

Perindopril erbumin (6.9 g; 78%) in an α form having a purity over 99% was obtained with individual impurities present in not more than 0.1% each.

The invention claimed is:

1. Process for the preparation of perindopril of the formula I or of pharmaceutically acceptable salts thereof

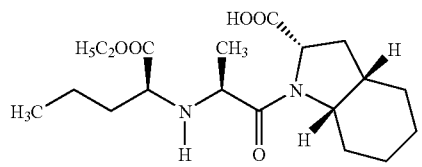

characterized in that a salt of the acid chloride of the formula III

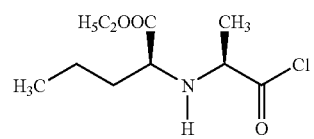

is reacted with (2S,3aS,7aS)-octahydroindole-2-carboxylic acid of the formula IV

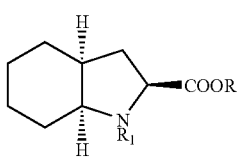

wherein R represents a trimethylsilyl group and R1 represents hydrogen or a protecting group, such as the trimethylsilyl group, to form a compound of the formula V

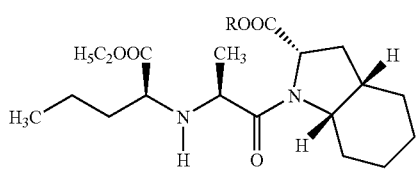

wherein R has the above meaning, which is converted to perindopril of the formula I by hydrolysis wherein the reaction for the formation of the peptide bond takes place in organic solvents, such as acetone, acetonitrile, dioxin, chloroform, methylene chloride, tetrahydrofuran or in a combination thereof with water, in the presence of a base.

2. Process according to claim 1 wherein the acid chloride of the formula III

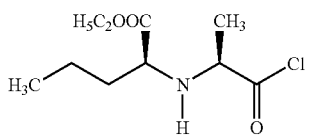

is prepared by conversion of N-((S)-1-carbethoxybutyl)-L-alanine of the formula II

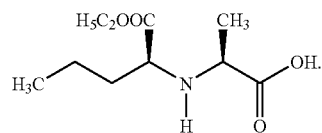

3. Process according to claim 1, wherein the hydrochloride salt of the acid chloride III is used.

4. Process according to claim 1, wherein the reaction for the formation of the peptide bond takes place in the temperature range of from −20° C. to +20° C., preferably at a temperature of from 0° C. to −20° C.

5. The method of claim 1, further comprising the step of:
treating the compound (V) with t-butylamine to produce perindopril erbumine.

\* \* \* \* \*